United States Patent [19]
Kupershmidt et al.

[11] Patent Number: 5,515,163
[45] Date of Patent: May 7, 1996

[54] METHOD AND APPARATUS FOR DETECTION, ANALYSIS AND IDENTIFICATION OF PARTICLES

[75] Inventors: Vladimir Kupershmidt, Pleasanton; Mikhail Kouchnir, Palo Alto, both of Calif.

[73] Assignee: Sunshine Medical Instruments, Inc., Sausalito, Calif.

[21] Appl. No.: 299,896

[22] Filed: Sep. 1, 1994

[51] Int. Cl.$^6$ .................................................. G01N 21/00
[52] U.S. Cl. ........................... 356/338; 356/339; 356/369
[58] Field of Search ...................... 356/336–343, 356/364, 368, 369, 349, 237, 365, 128; 250/225, 574, 575, 573

[56] References Cited

U.S. PATENT DOCUMENTS

| | | | |
|---|---|---|---|
| 4,071,298 | 1/1978 | Falconer | 356/336 |
| 4,251,733 | 2/1981 | Hirleman, Jr. | 250/575 |
| 4,477,187 | 10/1984 | Pettit et al. | 356/335 |
| 4,540,283 | 9/1985 | Bachalo | 356/336 |
| 4,636,075 | 1/1987 | Knollenberg | 356/336 |
| 4,764,013 | 8/1988 | Johnston | 356/338 |
| 4,796,995 | 1/1989 | Salzman et al. | 356/338 |
| 4,854,705 | 8/1989 | Bachalo | 356/336 |
| 4,890,925 | 1/1990 | Kitamori et al. | 356/336 |
| 4,893,932 | 1/1990 | Knollenberg | 356/338 |
| 4,953,980 | 9/1990 | DeVolk et al. | 356/338 |
| 4,986,659 | 1/1991 | Bachalo | 356/336 |
| 5,037,202 | 8/1991 | Batchelder et al. | 356/336 |
| 5,061,070 | 10/1991 | Batchelder et al. | 356/345 |
| 5,101,113 | 3/1992 | Hirleman, Jr. et al. | 250/574 |
| 5,133,602 | 7/1992 | Batchelder et al. | 356/375 |

OTHER PUBLICATIONS

Batchelder, J. S. and M. A. Taubenblatt, "Interferometric detection of forward scattered light from small particles", *Appl. Phys. Lett.*, 55 (3), Jul. 1989, pp. 215–217.

Batchelder, J. S. and M. A. Taubenblatt, "Real-time Single Particle Composition Detection *Liquids*", *Solid State Technology*, Oct. 1992.

Van de Hulst, H. C., *Light Scattering by Small Parricles*, New York: John Wiley & Sons, Inc., 1957, pp. 35–36.

Primary Examiner—Hoa Q. Pham
Attorney, Agent, or Firm—Orrick Herrington & Sutcliffe

[57] ABSTRACT

A method and an apparatus for the analysis of particles contained in a material, such as particles in a fluid or on a surface, such as the surface of a semiconductor, by two orthogonally polarized, intensity and phase modulated laser beams, wherein the detected scattered light is synchronously demodulated. The apparatus comprises a laser source producing a polarized laser beam, a state of polarization modulator, and a photoreceiver for detecting light scattered by particles at an angle to the incident light. A synchronous demodulator, such as a dual channel lock-in amplifier, separates the intensity and phase modulated portions of the scattered signals. A reference unit for detecting a non-scattered light produced by the sample to provide a reference is preferably provided, as well. The size, index of refraction and identity, of the particles, for example, can be determined.

42 Claims, 5 Drawing Sheets

METHOD AND APPARATUS FOR DETECTION, ANALYSIS AND IDENTIFICATION OF PARTICLES

FIELD OF THE INVENTION

The present invention relates to the detection, analysis and identification of particles, and, more particularly, to a dark field analysis configuration using intensity and phase modulated, orthogonally polarized components of a laser beam and synchronous demodulation of the detected, scattered light.

BACKGROUND OF THE INVENTION

Several instruments and methods for analyzing particles by measuring the phase shift of an incident laser beam scattered by particles are known. These methods consider a particle as a phase object and measure the effect of the particle on a waveform. Some of these instruments and methods conduct measurements in the so-called "bright field," others in the "dark field". A bright field configuration detects light scattered in the forward direction. A dark field configuration detects light scattered at an angle to the incident beam.

Light scattered in a forward direction by a small particle causes a phase shift and an attenuation of the incident beam dependent on the size and index of refraction of the particle. In U.S. Pat. No. 5,133,602, "Particle Path Determination System," by J. S. Batchelder et al., U.S. Pat. No. 5,061,070, "Particulate Inspection of Fluids Using Interferometric Light Measurements," by J. S. Batchelder, et al., and U.S. Pat. No. 5,037,202, "Measurements of Size and Refractive Index of Particles Using the Complex Forward-Scattered Electromagnetic Field," by J. S. Batchelder, et al., phase shift and extinction of a pair of orthogonally polarized laser beams are employed to characterize particles in the fluid. The forward direction of the scattered light is detected using an interferometer which measures the phase shift of one beam relative to another.

A different technique is employed for analyzing a particle in a dark field configuration. In U.S. Pat. No. 4,540,283 to Bachalo, for example, a dark field system is described in which two incident beams are crossed to set up an interference pattern that creates a varying electrical signal from changing fringes when a particle passes across the pattern. U.S. Pat. No. 4,764,013 to Johnston describes a dark field method that determines the phase difference between two polarization components of scattered light. Batchelder et al.s' U.S. Pat. No. 5,061,070, discussed above, also states that a dark field arrangement using a heterodyne interferometer, where a sample beam and a reference beam are provided having different wavelengths, can be used with its phase shift analysis technique.

In both bright and dark field particle detection systems, it is very important to know the dependence of the measured signal on the particle's trajectory in the vicinity of the laser beam profile.

Because most dark field optical configurations employ focused-beam geometry, it is also important to characterize the intensity distribution of the laser beam in a sampling volume or surface to be analyzed in order to determine the size of particles. Beam profile non-uniformity can cause measurement errors.

A correction system utilizing two coaxial laser beams of orthogonal polarization, varying widths, and coincident focal planes, is described by Knollenberg in U.S. Pat. No. 4,636,075. Knollenburg's design requires that the signal from a tightly focused laser beam increase above a threshold before taking the signal from the wider beam to obtain a particle size. It is therefore limited in the minimum size particles it can detect.

U.S. Pat. No. 4,854,705 to Bachalo describes another dark field detection system wherein concentric beams of different focal spot size are used to determine a particle's trajectory.

Regardless of the phase measurement technique employed in the above patents, the phase shift measurement is based on the intensity of the scattered signal and does not provide heterodyne detection of the polarization states of polarized incident light scattered by a particle.

SUMMARY OF THE INVENTION

It is therefore an object of the invention to eliminate the above disadvantages of other analysis techniques and to provide a new method and apparatus for the detection, analysis and identification of particles which employs a dark field measurement configuration to detect particles and to determine their sizes and indices of refraction.

Another object of the invention is to provide a particle identification system using synchronous demodulation.

Still another object of the invention is to provide an analysis system using orthogonally polarized components of a laser beam having a known phase shift.

Yet another object of the invention is to provide a detection system capable of analyzing a large volume of liquid.

A further object of the invention is to provide a particle identification system which can operate in the reflection mode for detecting particles on the surface of solid substrates.

To achieve these and other advantages in accordance with the present invention, intensity and phase modulated orthogonally polarized light beams are scattered off particles, such as particles in a liquid or on a surface such as the surface of a semiconductor, and detected at an angle to the incident light. The detected scattered light is synchronously demodulated to determine the effects of scattering by the particles on the intensity and phase modulations of the light beam. The size, index of refraction, and identity of the particles, for example, can thereby be determined.

In accordance with one embodiment of the invention, a method of analyzing particles in a material is disclosed comprising generating an intensity modulated, polarized laser beam. The laser beam is split into two orthogonally polarized beams, which are phase shifted with respect to each other. The two phase-shifted beams are directed onto the material and light scattered by particles in the material at an angle to the two beams is detected. The detected light is then synchronously demodulated. The particles can be in a liquid, or on a surface, such as the surface of a semiconductor, for example.

In another embodiment of the invention, a method of analyzing particles in a material is disclosed comprising generating a polarized laser beam which is intensity modulated at a first frequency. The polarized laser beam is then split into two orthogonally polarized beams, phase shifted with respect to each other at a second frequency. The two orthogonally polarized, phase shifted laser beams are directed onto the material and the light scattered by particles in the material is detected at an angle to the two beams, at the first and second frequencies.

An apparatus for analyzing particles in a material is also disclosed comprising means for generating a polarized laser beam; means for applying current modulation to the means for generating; means for splitting the polarized laser beam into two orthogonally polarized laser beams; means for phase shifting the two orthogonally polarized laser beams with respect to each other; means for directing the phase shifted, orthogonally polarized laser beams onto the material; means for detecting scattered light produced by the particles; and means for synchronously demodulating the detected scattered light. The means for demodulating preferably comprises a dual channel lock-in amplifier.

In another embodiment of the invention, an apparatus for the analysis of particles in a material comprises a laser source which produces an intensity modulated, polarized laser beam. A phase modulator comprising a polarized beam splitter cube is provided, comprising a center, first and second adjacent sides, a first quarter-wave plate located adjacent the first side and a second quarter-wave plate adjacent the second side. A first mirror is located adjacent the first quarter-wave plate and a second mirror is located adjacent the second quarter-wave plate. The first and second mirrors are spaced from the center of the polarized beam splitter cube by different distances. The phase modulator splits the laser beam into two orthogonally polarized laser beams, phase shifted with respect to each other. A sampling cell comprising the material to be analyzed is provided and the two orthogonally polarized laser beams are incident upon the sampling cell. A photoreceiver detects light scattered by particles in the material; and a synchronous demodulator is operatively connected to the photoreceiver. The synchronous demodulator is preferably a dual channel lock-in amplifier. The sampling cell can contain a fluid or a surface, such as the surface of a semiconductor.

DETAILED DESCRIPTION OF THE INVENTION

Figure 1:
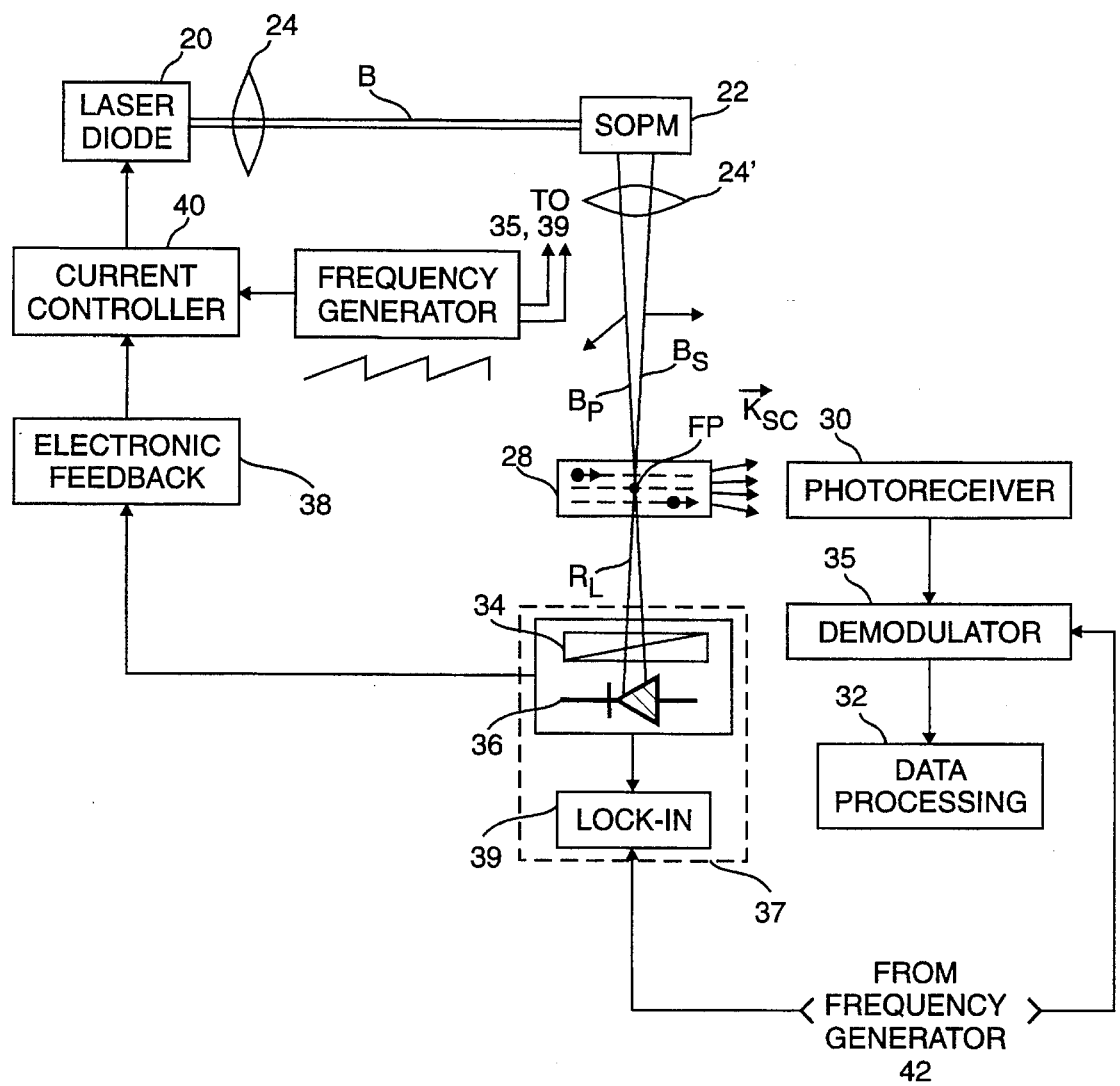
FIG. 1 is a block-diagram of an apparatus in accordance with a first embodiment of the present invention.

FIG. 1 is a block-diagram of an apparatus 10 for the detection, analysis and identification of particles in accordance with a first embodiment of the present invention. The apparatus of FIG. 1 comprises a laser source 20, a state-of-polarization phase modulator (SOPM) 22, a sampling cell 28, and a measuring photoreceiver 30.

The laser source 20 generates a polarized laser beam B. The laser source 20 is preferably a laser diode operating at the near-infrared wavelengths, and may be a Ga-As-type, single-frequency laser source, for example. Preferably, the laser source 20 operates at the shortest possible wavelengths, i.e., 650–680 µm. The laser diode 20 can be a model SDL-5400 G1, available from Spectra Diode Labs, Inc., San Jose, Calif., for example.

The output of the laser source 20 is intensity modulated and the effect of scattering by particles on the intensity modulated light beam is one of the scattering effects used to analyze the particles in accordance with the present invention. A frequency generator 42, which is preferably an arbitrary waveform generator, and a current controller 40 are preferably provided to modulate the intensity of the output of the laser source 20. The frequency generator 42 preferably provides a sawtooth waveform to the current controller 40, which drives the laser source 20 with a current modulated by the output of the frequency generator 42. Other suitable waveforms, such as a triangular waveform, can be used as well. The output of the laser source 20 is an intensity modulated, polarized laser beam B, whose intensity follows the sawtooth pattern of the frequency generator 40.

The preferred frequency of the output of the frequency generator 42 depends on the size of the particles to be analyzed. For example, to detect particles having diameters of about 10 microns, about 1 kHz is preferred. To detect particles have diameters less than 10 microns and greater than 1 micron, about 50 kHz is preferred. To detect particles having diameters less than about 1 micron, about 100 kHz is preferred.

The intensity modulated, polarized laser beam B is incident upon the SOPM 22, which splits the laser beam B into two superimposed, orthogonally polarized laser beams $B_S$ and $B_P$, phase shifted with respect to each other. The effect of scattering by a particle on the phase modulation of the two orthogonally polarized laser beams is also used to analyze particles in accordance with the present invention. A focusing lens 24' is preferably located between the laser source 20 and the SOPM 22. The configuration of the SOPM 22 is described further, below.

The intensity and phase modulated orthogonal laser beams $B_S$ and $B_P$ are directed onto the sample cell 28. A focusing lens 24' is preferably provided to focus the laser beams $B_S$ and $B_P$ onto a focal point FP within the sample cell 28. The sample cell 28 contains a liquid or a surface, such as the surface of a semiconductor wafer, as discussed with respect to FIG. 7, below. A particle passing through the focal point FP will scatter the laser beams $B_S$ and $B_P$. The effect of scattering on both the intensity and phase modulations of the beams $B_S$ and $B_P$ are used to analyze the particles, as discussed further, below.

Depending on whether the apparatus 10 is intended for measuring single events (identification of single particles of small size) or for inspecting large volumes of liquids, different beam profiles can be used for laser beams $B_S$ and $B_P$. The beam profile can be varied by suitable optics, as is known in the art. For single events, it is preferable to use a focused laser beam to increase the scattering signal intensity, while for inspection of large volumes, it is preferable to use a less focused laser beam.

The measuring photoreceiver 30 of FIG. 1 detects the scattered components of the incident beams $B_S$ and $B_P$. The photoreceiver 30 is located in a dark field position near the sample cell 28 at an angle θ between about 35°–135° with respect to the direction of propagation of the laser beams $B_S$ and $B_P$. To detect particles of less than 0.5 microns with a laser beam having a wavelength less than 1.0 micron, for example, an angle of about 90° is preferred.

The measuring photoreceiver 30 is connected to a synchronous demodulator 35, such as a dual-channel lock-in amplifier, which analyzes the detected signals. The amplitude and phase of the scattered light are analyzed at the frequencies of the intensity and phase modulations of the laser beam B. A single channel lock-in amplifier which is rapidly switched between the frequencies of the intensity and phase modulations, can also provide essentially synchronous demodulation, as discussed further below. Other suitable digital or analog demodulation techniques may be used, as well. A data processing unit 32 is connected to the lock-in amplifier 35. The data processing unit 32 can also be part of the lock-in amplifier. The photoreceiver is described in more detail with respect to FIGS. 5A and 5B, below.

The apparatus 10 can include a reference unit 37 which contains a polarizer 34, a photoreceiver 36 and a lock-in amplifier 39. The lock-in amplifier 39 has a low-frequency output which is connected to an electronic feedback unit 38. The feedback unit 38 is connected to the current controller 40. The current controller 40 may contain a temperature controller (not shown) to stabilize the temperature of the laser source 20. A reference beam RL, which is the direct incident light passing through the sampling cell 28, is detected by the reference photoreceiver 36 while the light $K_{SC}$ scattered by particles in the sampling cell 28 is detected by the photoreceiver unit 30 in the dark field position. In response to the reference beam RL, the reference photoreceiver 36 generates an electrical signal which is sent to an input of the electronic feedback 38. The feedback 38 then generates a low-frequency signal which is used to stabilize the phase of the orthogonally polarized optical beams $B_S$ and $B_P$ output by the SOPM 22 in a known manner. Instead of the reference unit 37, phase stabilization can be provided by suitable software, as is known in the art.

Inputs of both lock-in amplifiers 35 and 39 are preferably connected to an output of the frequency generator 42, which provides a stable reference signal to those amplifiers.

Figure 2:
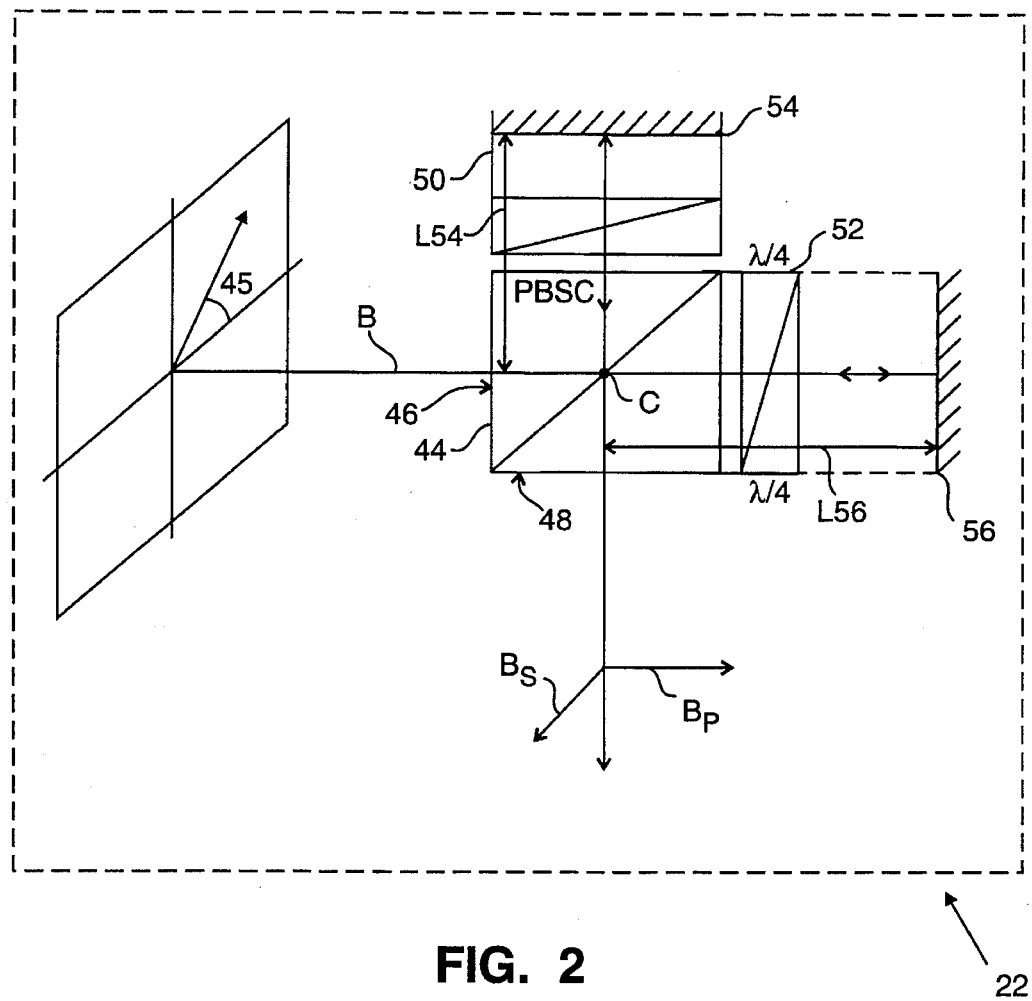
FIG. 2 is a schematic structural view of a state-of-polarization modulator used in the apparatus of FIG. 1.

The structure of the SOPM 22 is shown in FIG. 2. The SOPM 22 comprises a polarized-beam splitter cube (PBSC) 44 which has a beam input side 46 and a beam output side 48. The PBSC 44 splits the polarized beam B into the two superimposed beams $B_S$ and $B_P$, with orthogonal polarization, preferably with a 50/50 ratio. The PBSC 44 also causes a phase shift between the beams $B_S$ and $B_P$, due to the changing frequency of the output of the laser source 20 caused by the current modulation. The beams $B_S$ and $B_P$ propagate in the same direction. Beam $B_S$, which is a so-called S-polarized beam, has a polarization direction perpendicular to the plane of incidence (i.e., to the plane of the drawing). The S-polarized beam is also known as a vertical component. The beam $B_P$ is a so-called P-polarized beam, having a direction of polarization which lies in the plane of incidence (i.e., in the plane of the drawing). The P-polarized beam $B_P$ is also known as a horizontal component.

Located on two adjacent sides of the PBSC 44 are quarter-wave plates 50 and 52. A quarter-wave plate is a well known optical element which introduces a phase delay to an optical signal equal to one quarter of its wavelength. The quarter wave plates have a fast axis and a slow axis. Each quarter-wave plate 50 and 52 is oriented in the direction of their fast axes so that they form a 45° angle with respect to the direction of the polarization beams $B_S$ and $B_P$.

In FIG. 2 the plates 50 and 52 are shown separated from the PBSC 44. In the actual construction of the SOPM 22 they may be cemented or bonded to its respective sides. Located adjacent each quarter-wave plate 50 and 52 are mirrors 54 and 56, respectively. The distance between the mirrors 54 and 56 and the center C of the PBSC 44 are indicated as L54 and L56 in FIG. 2, respectively. The difference in length between L54 and L56 is maintained at a value less than the coherent length of the output of the laser source 20. In order to achieve a desired accuracy on the order of a few millidegrees, it is desirable that the difference between L54 and L56 be less than 0.5 mm. One of the mirrors, mirror 54 for example, is attached to the quarter-wave plate 50; the other mirror, mirror 56 for example, is separated from it's quarter-wave plate 52. The one mirror can be cemented to the quarter wave-plate, for example.

Suitable optical components, such as the PBSC 44, the quarter-wave plates 50, 52 and the mirrors, are available from Meadowlark Optics, Inc., Longmont, Calif., for example.

Figure 3:
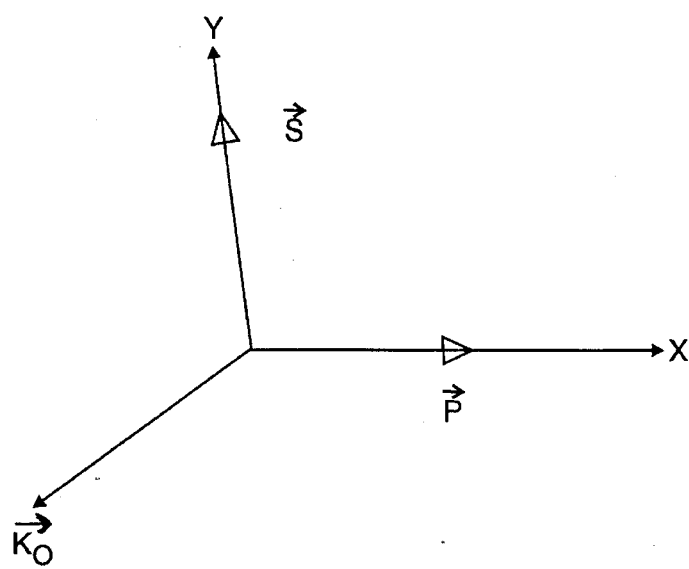
FIG. 3 shows a coordinate system and the direction of polarization vectors for output beams operating in the system of FIG. 1.

FIG. 3 shows a coordinate system with axes X and Y, and the direction of the polarization vectors of the output beams $B_S$ and $B_P$ produced by the SOPM 22.

The beams $B_S$ and $B_P$ have a phase shift F which is determined by the difference between the distance from the two mirrors 54 and 56 to the center C of the PBSC 44, as well as the amplitude of current modulation of the current controller 40 and the modulation frequency of the sawtooth waveform generated by the frequency generator 42. The total phase shift F is expressed by the following formula:

$$F(t) = 2\pi \frac{\Delta L \beta I_a f_o t}{c} - 2\pi f t, \quad (1)$$

where c is the velocity of light, $\Delta L$ is a geometrical path length difference between the optical center C of the PBCS 44 and respective mirrors 54 and 56 (the difference between L54 and L56), $\beta$ is the efficiency of modulation (frequency to current conversion factor), $I_a$ is an amplitude of current modulation, $f_o$ is the modulation frequency, and f is a phase modulation frequency. Thus, the SOPM 22 functions as an electro-optical converter which converts the electrical sawtooth waveforms generated by the frequency generator 42 to phase shifted sinusoidal waveforms.

Figure 4:
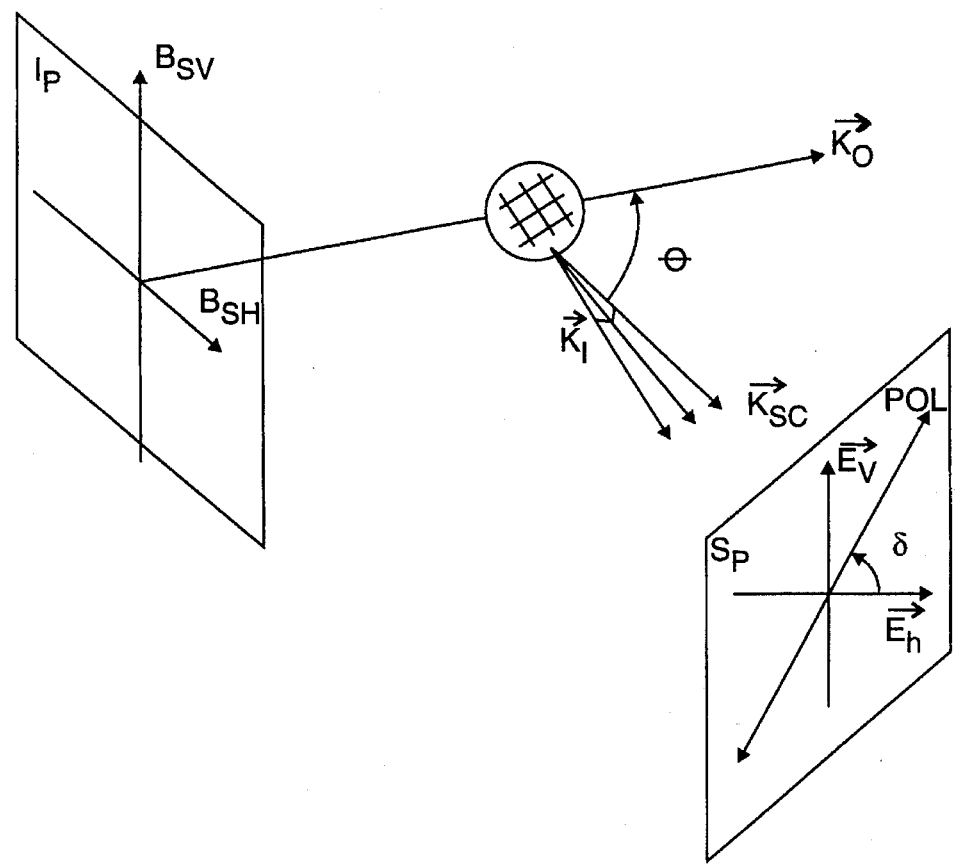
FIG. 4 shows the geometry of scattered polarized light.

The geometry of the scattering of beams $B_S$ and $B_P$ off a particle is shown schematically in FIG. 4. An incidence plane $I_P$ contains a vertical component $B_{SV}$ and a horizontal component $B_{PH}$ of the laser beams $B_S$ and $B_P$, respectively. When a particle P intersects the laser beams $B_S$ and $B_P$ propagating in the direction of unit vector $K_0$, the beams are scattered by the particle. One of the possible scattered beams $K_{SC}$ propagates in the direction of a unit vector $K_1$, toward the photoreceiver 30, at the scattering angle $\theta$ with respect to the vector $K_0$. The plane which contains vectors $K_0$ and $K_{SC}$ is called a scattering plane $S_P$. The scattered beam $K_{SC}$ has a vertical component $E_V$ and a horizontal component $E_H$ in the scattering plane $S_P$. A vector POL designates the direction of polarization of the scattered beam $K_{SC}$, which forms an angle $\delta$ with the direction of vector $E_H$.

The relationship between the scattered polarized components $E_V$, $E_H$ and the incident polarized components $B_{SV}$ and $B_{PH}$ can be expressed by the following formula:

$$\begin{pmatrix} E_V \\ E_H \end{pmatrix} = \begin{pmatrix} S_V(\theta) & 0 \\ 0 & S_H(\theta) \end{pmatrix} \begin{pmatrix} B_{SV} \\ B_{PH} \end{pmatrix} \quad (2)$$

(see H. C. van der Hulst, *Light Scattering by Small Particles*, N.Y., 1957, pp. 35–36, incorporated by reference herein), where $S_V(\theta)$ and $S_H(\theta)$ are the amplitudes of the scattered horizontal and vertical components of the incident beams at the scattering angle $\theta$.

Figure 5A:
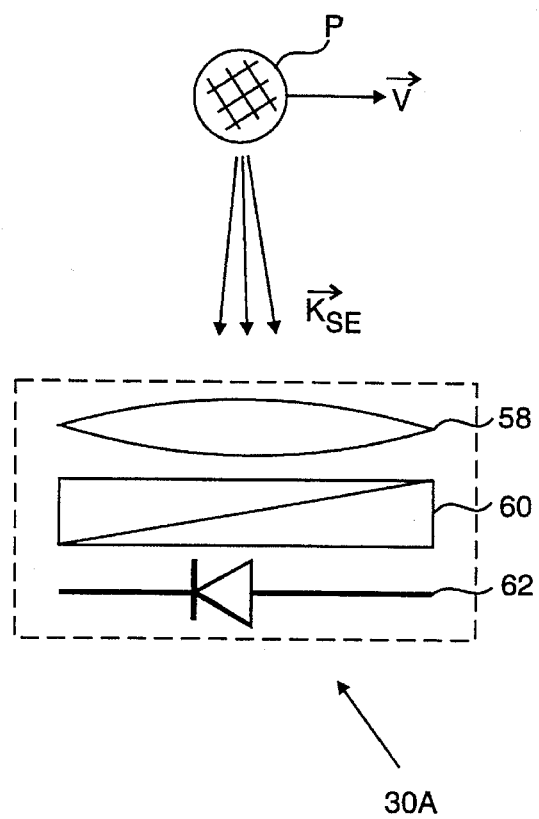
FIGS. 5A and 5B are two embodiments of preferred measuring photoreceivers for use in the apparatus of FIG. 1.
Figure 5B:
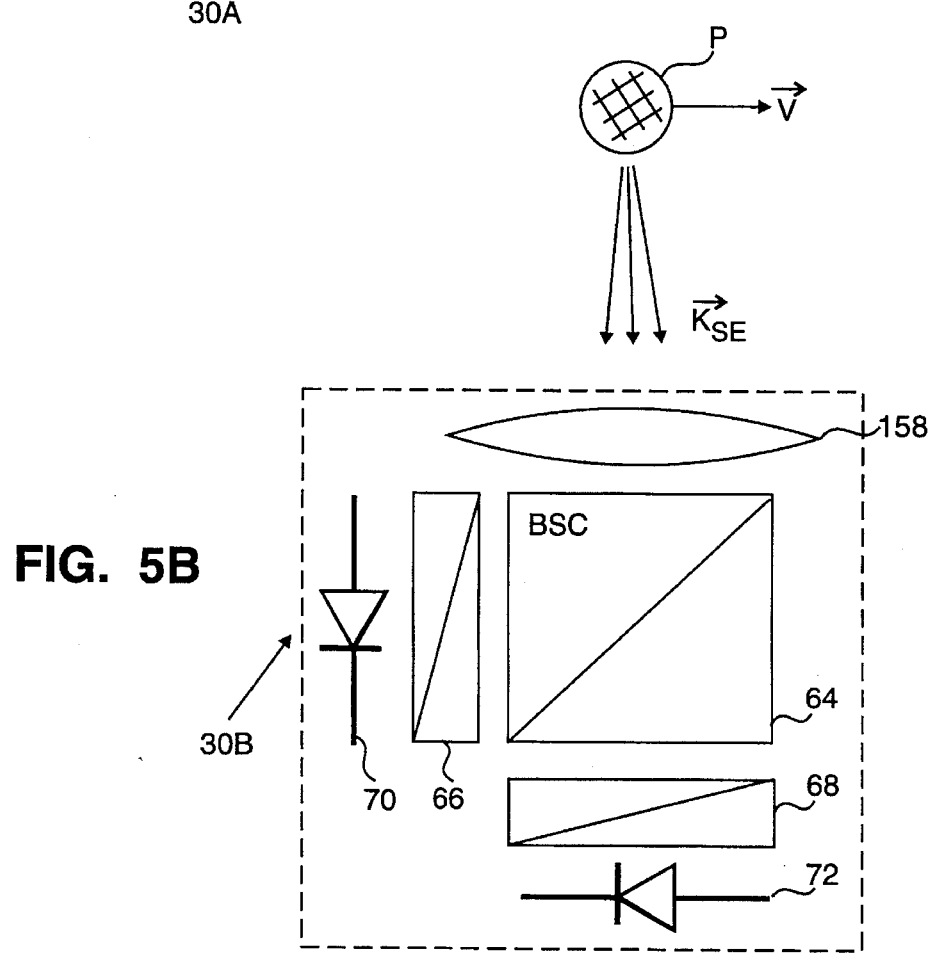

FIGS. 5A and 5B illustrate two photoreceivers 30A and 30B preferred for detecting the scattered beams $B_{SV}$, $B_{PH}$ in the apparatus 10 of the present invention. The measuring photoreceiver 30A in FIG. 5A preferably comprises a light-collecting lens 58 and a polarizer 60 oriented at an angle of δ=45° with respect to the directions of the vertical and horizontal components $E_V$ and $E_H$ of scattered beams $B_{SV}$ and $B_{PH}$, respectively. A photodetector 62 is positioned after the polarizer 60 in the direction of beam propagation, preferably operating at the modulation frequency of the frequency generator 42. Silicon photodiodes, model SD100-41-11-231, available from Advanced Photonics, Inc., are suitable photodetectors.

The photoreceiver 30B shown in FIG. 5B is more preferred. The measuring photoreceiver 30B comprises a light-collecting lens 158 and a beam splitter cube (BSC) 64 which receives light scattered by particles and propagating in the direction of vector $K_{SC}$. Located on adjacent sides of the BSC 64 are two polarizers 66 and 68 having axes of polarization oriented at angles of δ=45° and δ=−45°, respectively. Polarized scattered beams which pass through the polarizers 66 and 68 are received by the photodetectors 70 and 72, respectively. These photodetectors are of the same type as photodetector 62, described above.

It is understood that the measuring photoreceivers 30A and 30B contain appropriate electronic circuits (not shown) which are known in the art.

Returning to FIG. 1, as discussed above, the photoreceivers 30 are preferably connected to the dual channel lock-in amplifier 35. One channel of the lock-in amplifier measures the amplitude of the scattered signal at the frequency at which the light beam is intensity modulated, and the other measures the amplitude and phase of the scattered signal at the frequency at which the light beam is phase modulated. These measurements are made essentially simultaneously, to synchronously demodulate the detected light. The intensity modulation is preferably measured at the frequency of the output of the frequency generator 42, which depends on the size of the particles to be analyzed, as discussed above. The phase modulation is preferably measured at a frequency about ten (10) times the frequency of the output of the frequency generator 42, at the phase modulation frequency. For example, to detect particles of about 10 microns or larger, the output of the frequency generator and the frequency of one channel of the lock-in amplifier 35 is preferably 1 kHz, while the frequency of the other channel of the lock-in amplifier 35 is preferably 10 kHz.

Alternatively, a single channel lock-in amplifier can be used. In that case, the amplifier is preferably rapidly shifted (in the millisecond range) between the frequencies of the intensity and phase modulations, to obtain nearly simultaneous measurements. Such rapid measurements are sufficient to provide essentially synchronous demodulation of the scattered signals. As mentioned above, other methods of providing digital or analog synchronous demodulation may be employed, as well.

The data processing unit 32 is preferably a digital signal processor which processes signals received from the lock-in amplifier 35. As stated above, it may be part of the lock-in amplifier. A suitable lock-in amplifier which includes such a data processing unit is a model SR 850 DSP Lock-In Amplifier from Stamford Research Systems, Inc. The data processing unit 32 calculates the index of refraction and size of the particles, based on the scattered signals and known formulas. Index of refraction is one of the parameters used to identify materials, as is known in the art.

As discussed above, the electronic feedback unit 38 is provided for phase stabilization of the output of the laser source 20. The feedback unit 38 preferably comprises a conventional proportional integrated derivative (PID) controller (not shown), which comprises electronic circuitry operating in proportional, integrated, and derivative modes. The bandwidth frequency of the electronic feedback 38 is selected so that it satisfies the slow feedback condition:

$$\Delta B \ll 1/\tau$$

where ΔB is a feedback bandwidth and τ is time of residence of the particle within the boundaries of the laser beam. For the case of liquid flowing with velocity V, τ=D/V, where D is the laser beam diameter. The phase shift F of the laser beams $B_S$ and $B_P$ (formula (1)) is such that during time τ, the reference signal can execute many oscillations. In other words, 1/f≪τ, where f is the frequency of the reference signal. In practice, f is about 100/τ. This condition requires that if the particle is small or the velocity of the flow is high, the reference frequency must fall into a MHz frequency range. An advantage of the use of a laser diode as the laser source 20 is that it can be easily modulated in such a frequency range.

The apparatus of the present invention can be made in the form of a portable instrument that can be transported to a measurement site. It is, therefore, suitable for analyzing the contamination of liquid flowing through a pipeline, for example. The apparatus can be arranged so that the liquid to be analyzed flows through the sample cell 28.

The theory on which the principle of detection, analysis and identification of particles in accordance with the present invention is based, will now be discussed. As described above, the SOPM 22 converts the intensity modulated, polarized laser beam B into two superimposed orthogonal polarized beams $B_S$ and $B_P$, phase shifted with respect to each other. When a particle N which moves in a liquid sample of the sampling cell media passes through the focal point FP of the sample cell 28, both laser beams $B_S$ and $B_P$ are scattered. This scattering event is detected by the measuring photoreceiver 30, which produces an electrical measurement signal. With the photoreceiver 30A of FIG. 5A, given angles δ and θ (see FIG. 4), and a synchronous demodulation detection technique for determining the amplitude of the scattered light at the frequency of intensity modulation and the amplitude and phase of the scattered light at the frequency phase modulation, the intensity of the measured signal I(θ,δ) can be represented by the following formula:

$$I(\theta,\delta)=I_o(t)\ (|S_H|^2 \cos^2\delta+|S_V|^2 \sin^2\delta)+I_o|S_H||S_V| \sin 2\delta \cos (2\pi ft+\Delta(\theta)) \quad (3)$$

where:

$I_o(t)$ is the intensity modulation of the laser diode as a function of time;

$I_o$ is an amplitude of the intensity modulation;

$|S_V|$ and $|S_H|$ are amplitudes of the vertical and horizontal components of the scattered signals, respectively;

$\Delta(\theta)$ is the phase difference between the vertical component $S_V$ and the amplitude of the horizontal component $S_H$ caused by the scattering; and f is the phase modulation frequency.

With the photoreceiver 30B of FIG. 5B, the absolute value of $S_V$ and $S_H$ depend on the intensity distribution of the incident beams $B_S$ and $B_P$ in the sample cell 28. The signals produced by the photodetectors 70 and 72, respectively, can be expressed as follows:

$$I(\theta,\delta=°45)=I_o(t)(|S_H|^2+|S_V|^2)+I_o|S_H S_V| \cos (2\pi ft+\Delta\theta) \quad (4.1)$$

$$I(\theta,\delta=-°45)=I_o(t)(|S_H|^2+|S_V|^2)- I_o|S_H S_V| \cos (2\pi ft+\Delta\theta) \quad (4.2)$$

Because the amplitude of the scattered signal $S_H$ is much smaller than the amplitude of the scattered signal $S_V$, expressions 4.1 and 4.2 can be respectively rewritten as follows:

$$I(\theta, \delta=+°45)=I_o(t)\ |S_H|^2+I_o|S_H S_V|\ \cos(2\pi ft+\Delta\theta) \quad (5.1)$$

$$I(\theta, \delta=-°45)=I_o(t)\ |S_H|^2-I_o|S_H S_V|\ \cos(2\pi ft+\Delta\theta) \quad (5.2)$$

It is apparent from formulas 4.1–4.2 and 5.1–5.2, that the first term of each formula corresponds to a first signal which can be detected at the frequency of intensity modulation and the second term corresponds to a second signal which can be detected at the frequency of phase modulation. A dual channel lock-in amplifier (or a rapidly switching single channel lock-in amplifier) at those frequencies provides simultaneous (or near simultaneous) measurement of those signals, as discussed above. Such simultaneous or near simultaneous measurements enables the determination of the amplitudes $S_V$ and $S_H$ and the absolute phase shift between these amplitudes. A further advantage of the photoreceiver 30B of FIG. 5B, is that two photoreceivers 70 and 72 each measure the amplitude of the first signal and the amplitude and phase of the second signal, simultaneously at two different polarizations.

Simple electronic circuitry can produce a ratio of the amplitude of the second signal to that of the first signal. Since the particle P interacts with both beams $B_S$ and $B_P$ simultaneously, this ratio does not depend on the position or trajectory of the particle P within the laser beams. Both the amplitude and phase shift depend on the size and index of refraction of the particle, and the wavelength and intensity of the laser beam B.

As can be seen from formula (5), by subtracting $I(\theta, \delta=45°)$ from $I(\theta, \delta=-45°)$, one can obtain an exact value of the second signal, particularly its phase and its amplitude. Such subtraction makes it possible to eliminate common optical noise which is always present in dark field particle detection system.

Figure 6:
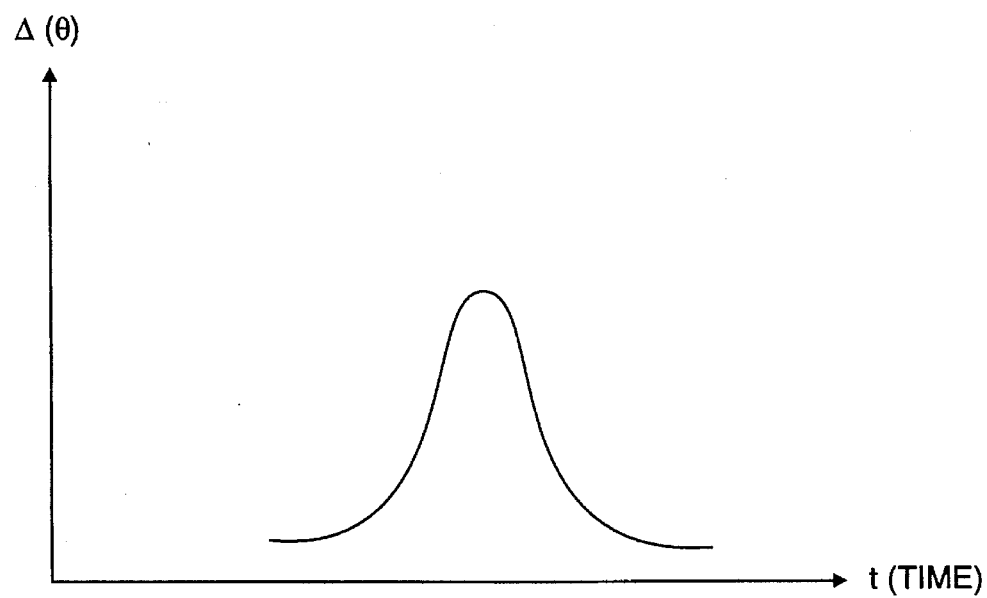
FIG. 6 is a graphical representation of the phase shift caused by particle scattering in the present invention.

Since beams $B_S$ and $B_P$ follow the same optical path, the particle which scatters the light will produce a phase shift represented by a signal of one polarity, as shown in FIG. 6. This means that if more than one particle is located within the boundaries of the beams $B_S$ and $B_P$, the signal produced by these particles will never eliminate each other but will only make the phase shift signal broader. This enables averaged measurements which are necessary if the sampling cell 28 contains a high density distribution of particles.

As an example, if water (with a refraction index of $N_o=1.33$) which passes through the sampling cell 28 is contaminated with particles of $SiO_2$ having a 0.1 μm diameter and an index of refraction N equal to 1.43, the phase shift produced by the scattered laser light having wavelength 0.86 μm (at $\theta=90°$) will be equal to 1.14°.

If the photoreceiver 30A of FIG. 5A is used, the amplitude of the scattered signal is proportional to $|S_V \cdot S_H|$ (see formula 3). As shown in formula 3, the electrical signal detected in this embodiment can also be represented by a first signal detected at the frequency of intensity modulation and a second signal detected at the frequency of phase modulation. Since both the amplitude and phase shift of the signals depend on the size of the particle P and its index of refraction, it is possible to analyze and identify the particles which cause the scattering.

Figure 7:
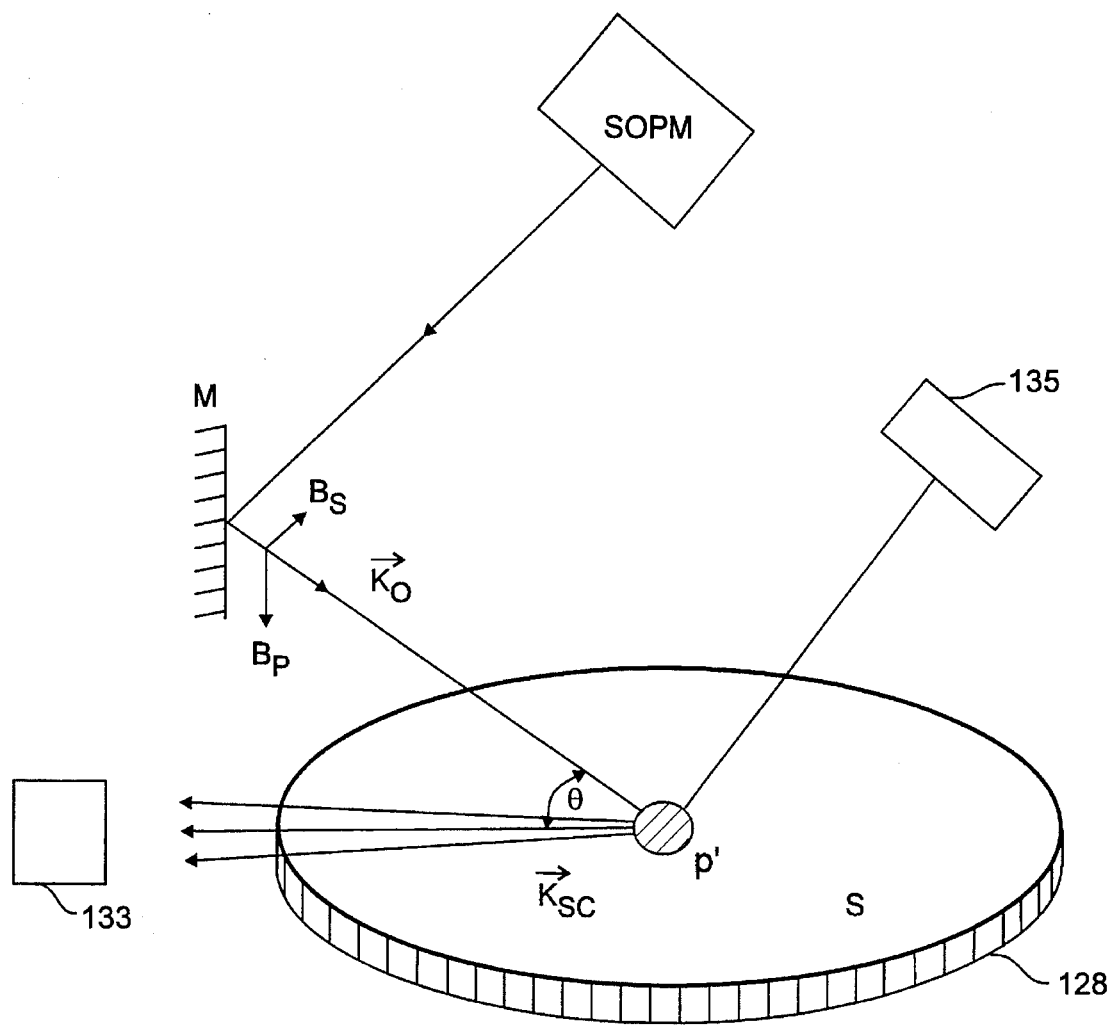
FIG. 7 is a partial illustration of a second embodiment of the present invention, for detecting particles on a surface.

The present invention can be used to detect particles on the surface of a substrate, as well. FIG. 7 shows a portion of a second embodiment of the invention, where the sample cell 28 of FIG. 1 is replaced by a solid substrate 128, which in the illustrated case has a flat surface S. The laser diode 20, current controller 40 and frequency generator 42 of FIG. 1 are used to generate an intensity modulated polarized laser beam. Those components are not shown in FIG. 7. A mirror M is installed at an angle to the direction of incident beams $B_S$ and $B_P$ which are emitted from the SOPM 22 of FIG. 1. The mirror M is designed to direct the laser beams $B_S$ and $B_P$ to the surface S at an angle. A photoreceiver unit 133 (which can be either of the photoreceivers of FIG. 5A or FIG. 5B), is in a dark field position to detect the light scattered by a particle P on the surface S, in the direction of unit vector $K_O$, at an angle $\theta$ to the incident beams. A reference unit 135 (which is the same as the reference unit 35 of FIG. 1) is preferably provided, positioned to receive the light specularly reflected from the surface S, itself. The electronic feedback 38 of FIG. 1 (not shown in FIG. 7) is also preferably provided for phase stabilization, as discussed above. Preferably, the solid substrate is supported on a platform which can move the substrate 128 with respect to the incident laser beams $B_S$ and $B_P$, so that the entire surface of the substrate can be examined. Alternatively, the mirror M can be a scanning mirror whose angle can be changed to reflect the laser beams $B_S$ and $B_P$ across the surface of the substrate. Suitable control can be provided to control the movement of the mirror M, as is known in the art. The position of the reference unit 135 needs to move as the angle of the incidence of the beams $B_S$ and $B_P$ is changed, so that it will continue to receive reflected light.

The analysis of the signals detected by the photodetector 130 are the same as in the apparatus of FIG. 1.

One skilled in the art will appreciate that the present invention can be practiced by other than the described embodiments, which are provided for purposes of illustration and not of limitation.

We claim:

1. A method of analyzing particles in a material, the method comprising:

generating an intensity modulated, polarized laser beam;

splitting the laser beam into two orthogonally polarized beams, phase shifted with respect to each other;

directing the two phase-shifted beams onto the material;

detecting light scattered by particles in the material at an angle to the two beams; and synchronously demodulating the detected scattered light.

2. The method of claim 1, wherein the polarized laser beam is generated by a laser diode operating at a given laser current.

3. The method of claim 2, wherein the splitting step comprises modulating the intensity of the laser current and converting the current modulation into phase modulation.

4. The method of claim 3, wherein the laser current is modulated by a sawtooth waveform, which, after phase modulation has a sinewave form.

5. The method of claim 1, wherein the splitting step comprises directing the polarized laser beam onto a polarized beam splitter cube comprising a center, first and second adjacent sides, a first quarter wave plate located on the first side and a second quarter wave plate located on the second side, a first mirror located adjacent the first quarter wave plate and a second mirror located adjacent the second quarter wave plate, the mirrors being spaced from the center of said polarized beam splitter cube by different distances.

6. The method of claim 1, wherein the step of directing the two phase-shifted beams further comprises directing the beams into a liquid.

7. The method of claim 6, further comprising detecting non-scattered light which passes through the liquid and using the detected non-scattered light as a reference.

8. The method of claim 7, further comprising stabilizing the phase of the phase shifted laser beams based on the reference.

9. The method of claim 1, further comprising splitting the detected scattered light into two beams and separately detecting the two beams.

10. The method of claim 1, wherein the material is a solid substrate having a surface and the particles to be analyzed are on the surface.

11. The method of claim 10, further comprising directing the two phase shifted beams onto the surface of the substrate at an angle.

12. The method of claim 11, further comprising detecting light reflected from the surface for use as a reference.

13. The method of claim 11, further comprising moving the substrate with respect to the beams.

14. The method of claim 11, further comprising a directing the beams across the surface of the substrate with a mirror.

15. The method of claim 1, wherein the synchronous demodulation step comprises detecting the scattered light at a first and second frequency essentially simultaneously.

16. The method of claim 15, wherein the first frequency is a frequency of intensity modulation of the scattered light and the second frequency is a frequency of phase modulation of the scattered light.

17. The method of claim 1, further comprising determining the amplitudes and additional phase shift of the detected scattered light.

18. A method of analyzing particles in a material, the method comprising:
    generating a polarized laser beam;
    modulating the intensity of the polarized laser beam at a first frequency;
    splitting the polarized laser beam into two orthogonally polarized beams;
    phase shifting the two polarized laser beams with respect to each other at a second frequency;
    directing the two orthogonally polarized, phase shifted laser beams onto the material; and
    detecting light scattered by particles in the material at an angle to the two beams, at the first and second frequencies.

19. The method of claim 18, further comprising simultaneously measuring the amplitude and phase of the light scattered by the particles at the first and second frequencies.

20. A method of analyzing particles on the surface of a semiconductor, the method comprising:
    generating a polarized laser beam; modulating the intensity of the polarized laser beam at a first frequency;
    splitting the polarized laser beam into two orthogonally polarized beams;
    phase shifting the two polarized laser beams with respect to each other at a second frequency;
    directing the two orthogonally polarized, phase shifted laser beams onto the surface of the semiconductor;
    detecting light scattered by particles on the surface of the semiconductor at an angle to the two beams; and
    synchronously demodulating the detected scattered light.

21. An apparatus for analyzing particles in a material, the apparatus comprising:
    means for generating a polarized laser beam;
    means for applying current modulation to the means for generating;
    means for splitting the polarized laser beam into two orthogonal polarized laser beams;
    means for phase shifting the two orthogonally polarized laser beams with respect to each other;
    means for directing the phase shifted, orthogonally polarized laser beams onto the material;
    means for detecting scattered light produced by the particles; and
    means for synchronously demodulating the detected scattered light.

22. The apparatus of claim 21, wherein the means for detecting comprises a polarizer oriented at an angle of 45° with respect to vertical and horizontal components of scattered light, and a photodetector.

23. The apparatus of claim 21, wherein the means for splitting and the means for phase shifting comprises a polarized beam splitter cube comprising a center, first and second adjacent side, a first quarter-wave plate located adjacent the first side and a second quarter-wave plate located on the second side, a first mirror located adjacent the first quarter-wave plate and a second mirror located adjacent the second quarter-wave plate, the first and second mirrors being spaced from the center of the polarized beam splitter cube by different distances.

24. The apparatus of claim 21, wherein the means for detecting comprises at least one polarizer and at least one photodetector.

25. The apparatus of claim 24, wherein the means for detecting further comprises:
    a beam splitter cube comprising first and second adjacent sides;
    a first polarizer located adjacent the first side and a second polarizer located adjacent the second side, the first and second polarizers having axes of polarization oriented at angles of approximately 45° and −45°, respectively; and
    a first photodetector for detecting scattered beams which pass through the first polarizer and a second photodetector for detecting scattered beams which pass through the second polarizer.

26. The apparatus of claim 25, wherein the means for demodulating comprises a dual channel lock-in amplifier operatively connected to the photodetector.

27. The apparatus of claim 25, wherein the means for demodulating comprises a lock-in amplifier which can be rapidly switched between at least two frequencies.

28. The apparatus of claim 21, wherein the means for demodulating comprises a dual channel lock-in amplifier operatively connected to the photodetector.

29. The apparatus of claim 21, wherein the means for demodulating comprises a lock-in amplifier which can be rapidly switched between at least two frequencies.

30. The apparatus of claim 21, further comprising a reference means for detecting non-scattered light produced by the material.

31. The apparatus of claim 21, wherein the material is a liquid and the apparatus further comprises a sampling cell adapted for the passage of the liquid.

32. The apparatus of claim 21, wherein the material is a solid substrate having a flat surface containing the particles.

33. The apparatus of claim 32, wherein the means for directing the phase shifted, polarized beams onto the material, directs the beams onto the material at an angle.

34. The apparatus of claim 33, wherein the means for directing comprises a mirror and the phase shifted, orthogonally polarized beams are directed onto the mirror, which directs the beams onto the substrate at an angle.

35. The apparatus of claim 34, wherein the mirror can scan the beams across the surface of the substrate.

36. The apparatus of claim 35, further comprising reference means for receiving light reflected off the surface of the substrate.

37. An apparatus for the analysis of particles in a material, the apparatus comprising:

- a laser source producing an intensity modulated, polarized laser beam;
- a phase modulator comprising a polarized beam splitter cube comprising a center, first and second adjacent sides, a first quarter-wave plate located adjacent the first side and a second quarter-wave plate adjacent the second side, a first mirror adjacent the first quarter-wave plate and a second mirror adjacent the second quarter-wave plate, the first and second mirrors being spaced from the center of the polarized beam splitter cube by different distances, wherein the phase modulator splits the laser beam into two orthogonally polarized laser beams, phase shifted with respect to each other;
- a sampling cell comprising the material to be analyzed, wherein the two orthogonally polarized laser beams are incident upon the sampling cell;
- a photoreceiver for detecting light scattered by particles in the material; and
- a synchronous demodulator operatively connected to the photoreceiver.

38. The apparatus of claim 37, wherein the synchronous demodulator comprises a dual channel lock-in amplifier.

39. The apparatus of claim 37, wherein the synchronous demodulator comprises a lock-in amplifier which can be rapidly switched between at least two frequencies.

40. The apparatus of claim 39, wherein the synchronous demodulator comprises a dual channel lock-in amplifier.

41. The apparatus of claim 39, wherein the synchronous demodulator comprises a lock-in amplifier which can be rapidly switched between at least two frequencies.

42. An apparatus for the analysis of particles on the surface of a semiconductor, the apparatus comprising:

- a laser source producing an intensity modulated, polarized laser beam;
- a phase modulator comprising a polarized beam splitter cube comprising a center, first and second adjacent sides, a first quarter-wave plate located adjacent the first side and a second quarter-wave plate adjacent the second side, a first mirror adjacent the first quarter-wave plate and a second mirror adjacent the second quarter-wave plate, the first and second mirrors being spaced from the center of the polarized beam splitter cube by different distances, wherein the phase modulator splits the laser beam into two orthogonally polarized laser beams, phase shifted with respect to each other;
- a sampling cell containing the semiconductor to be analyzed, wherein the two orthogonally polarized laser beams are incident upon the surface of the semiconductor;
- a photoreceiver for detecting light scattered by particles on the surface of the semiconductor; and
- a synchronous demodulator operatively connected to the photoreceiver.

* * * * *